US012642430B2

(12) United States Patent (10) Patent No.: US 12,642,430 B2
Sguigna et al. (45) Date of Patent: Jun. 2, 2026

(54) SYSTEMS AND METHODS TO MEASURE RETINAL PERFUSION

(71) Applicant: The Board of Regents of The University of Texas System, Austin, TX (US)

(72) Inventors: Peter V. Sguigna, Dallas, TX (US); Benjamin M. Greenberg, Dallas, TX (US); Darrel Conger, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 912 days.

(21) Appl. No.: 17/995,403

(22) PCT Filed: Apr. 2, 2021

(86) PCT No.: PCT/US2021/025624
§ 371 (c)(1),
(2) Date: Oct. 3, 2022

(87) PCT Pub. No.: WO2021/203029
PCT Pub. Date: Oct. 7, 2021

(65) Prior Publication Data
US 2023/0148862 A1     May 18, 2023

Related U.S. Application Data

(60) Provisional application No. 63/005,246, filed on Apr. 4, 2020.

(51) Int. Cl.
*A61B 3/12*     (2006.01)
*A61B 3/00*     (2006.01)
*A61B 5/00*     (2006.01)

(52) U.S. Cl.
CPC .......... *A61B 3/1233* (2013.01); *A61B 3/0025* (2013.01); *A61B 3/1241* (2013.01); *A61B 5/4088* (2013.01)

(58) Field of Classification Search
CPC ..... A61B 3/0025; A61B 3/102; A61B 3/1233; A61B 3/1241; A61B 5/4088
See application file for complete search history.

(56) References Cited

U.S. PATENT DOCUMENTS 5,360,010 A     11/1994  Applegate
2016/0183786 A1   6/2016  Wei et al.
(Continued)

FOREIGN PATENT DOCUMENTS

EP         2926722 A1    10/2015
WO      2018/237011 A1   12/2018

OTHER PUBLICATIONS

International Search Report and Written Opinion for PCT application No. PCT/US2021/025624, mailed on Jul. 19, 2021, 8 pages.
(Continued)

*Primary Examiner* — Jack Dinh
(74) *Attorney, Agent, or Firm* — POLSINELLI PC

(57)     ABSTRACT

Systems and methods for performing a retinal angiogram, which can be used to non-invasively quantify retinal perfusion by measuring differences in retinal vascular density. The systems and methods can be used to measure a response of the vasculature, particularly in the choriocapillaris. The systems and methods can be used to diagnose neurodegenerative conditions, associated sleep and mood disorders, and measure metabolic reserve. In particular, the systems and methods can also be used for both diagnostics and prognostics.

15 Claims, 9 Drawing Sheets

(56) References Cited

U.S. PATENT DOCUMENTS

2016/0228000 A1    8/2016    Spaide
2016/0262606 A1    9/2016    Mosaed et al.
2017/0319061 A1    11/2017    Spaide
2017/0347878 A1    12/2017    Milea et al.

OTHER PUBLICATIONS

Meltzer E, et al. Retinal Architecture and Melanopsin-Mediated Pupillary Response Characteristics: A Putative Pathophysiologic Signature for the Retino-Hypothalamic Tract in Multiple Sclerosis. JAMA Neurol. May 1, 2017;74(5):574-582. doi: 10.1001/jamaneurol. 2016.5131. PMID: 28135360; PMCID: PMC5822208.

Sikka, Gautam, et al. "Melanopsin mediates light-dependent relaxation in blood vessels." Proceedings of the National Academy of Sciences 111.50 (2014): 17977-17982.

Salter A, et al. The association of fatigue and social participation in multiple sclerosis as assessed using two different instruments. Mult Scler Relat Disord. Jun. 2019;31:165-172. doi: 10.1016/j.msard. 2019.04.014. Epub Apr. 13, 2019. PMID: 31063935.

Narayan RN, et al. Atypical Anti-MOG syndrome with aseptic meningoencephalitis and pseudotumor cerebri-like presentations. Mult Scler Relat Disord. Jan. 2019;27:30-33.

Lorefice L, et al. Assessing the burden of vascular risk factors on brain atrophy in multiple sclerosis: A case-control MRI study. Mult Scler Relat Disord. Jan. 2019;27:74-78.

Murphy OC, et al. Alterations in the retinal vasculature occur in multiple sclerosis and exhibit novel correlations with disability and visual function measures. Mult Scler. May 16, 2019:1352458519845116.

Green AJ, et al. Ocular pathology in multiple sclerosis: retinal atrophy and inflammation irrespective of disease duration. Brain. Jun. 2010;133(Pt 6):1591-601.

Nolan RC, et al. Optimal Intereye Difference Thresholds in Retinal Nerve Fiber Layer Thickness for Predicting a Unilateral Optic Nerve Lesion in Multiple Sclerosis. J Neuroophthalmol. Dec. 2018;38(4):451-458.

Martinez-Lapiscina EH, et al. Retinal thickness measured with optical coherence tomography and risk of disability worsening in multiple sclerosis: a cohort study. Lancet Neurol. May 2016;15(6):574-584.

Balcer LJ, et al. Multiple Sclerosis Outcome Assessments Consortium. Validity of low-contrast letter acuity as a visual performance outcome measure for multiple sclerosis. Mult Scler. Apr. 2017;23(5):734-747.

El Ayoubi NK, et al. Retinal measures correlate with cognitive and physical disability in early multiple sclerosis. J Neurol. Nov. 2016;263(11):2287-2295.

Toledo J, et al. Retinal nerve fiber layer atrophy is associated with physical and cognitive disability in multiple sclerosis. Mult Scler. Aug. 2008;14(7):906-912.

Chougule PS, et al. Light-Induced Pupillary Responses in Alzheimer's Disease. Front Neurol. Apr. 12, 2019;10:360.

Elman JA, et al. Task-evoked pupil dilation and BOLD variance as indicators of locus coeruleus dysfunction. Cortex. Dec. 2017;97:60-69.

Granholm EL, et al. Pupillary Responses as a Biomarker of Early Risk for Alzheimer's Disease. J Alzheimers Dis. 2017;56(4):1419-1428.

Ahmadi H, et al. Melanopsin-mediated pupillary light reflex and sleep quality in patients with normal tension glaucoma. Acta Ophthalmol. May 2019.

Blazek P, et al. Objective characterization of the relative afferent pupillary defect in MS. J Neurol Sci. Dec. 15, 2012;323(1-2):193-200.

Salter AR, et al. Retinal architecture predicts pupillary reflex metrics in MS. Mult Scler. Apr. 2009;15(4):479-486.

Park JC, et al. Toward a clinical protocol for assessing rod, cone, and melanopsin contributions to the human pupil response. Invest Ophthalmol Vis Sci. Aug. 22, 2011;52(9):6624-6635.

Tsujimura S, et al. Contribution of human melanopsin retinal ganglion cells to steady-state pupil responses. Proc Biol Sci. Aug. 22, 2010;277(1693):2485-2492.

Gamlin PD, et al. Human and macaque pupil responses driven by melanopsin-containing retinal ganglion cells. Vision Res. Mar. 2007;47(7):946-954.

Dumpala S, et al. Outer Retinal Structure and Function Deficits Contribute to Circadian Disruption in Patients With Type 2 Diabetes. Invest Ophthalmol Vis Sci. May 1, 2019;60(6):1870-1878.

Feigl B, et al. The post-illumination pupil response of melanopsin-expressing intrinsically photosensitive retinal ganglion cells in diabetes. Acta Ophthalmol. May 2012;90(3):e230-4.

Joyce DS, et al. Melanopsin-mediated pupil function is impaired in Parkinson's disease. Sci Rep. May 17, 2018;8(1):7796.

La Morgia C, et al. Retinal Ganglion Cells and Circadian Rhythms in Alzheimer's Disease, Parkinson's Disease, and Beyond. Front Neurol. May 4, 2017;8:162.

Weng S, et al. Circadian modulation of melanopsin-driven light response in rat ganglion-cell photoreceptors. J Biol Rhythms. Oct. 2009;24(5):391-402.

Chen SK, et al. Photoentrainment and pupillary light reflex are mediated by distinct populations of ipRGCs. Nature. Jul. 17, 2011;476(7358):92-95.

Zele AJ, et al. The circadian response of intrinsically photosensitive retinal ganglion cells. PLoS One. Mar. 14, 2011;6(3):e17860.

Brzezinski JA 4th, et al. Loss of circadian photoentrainment and abnormal retinal electrophysiology in Math5 mutant mice. Invest Ophthalmol Vis Sci. Jul. 2005;46(7):2540-2551.

Moura AL, et al. The pupil light reflex in Leber's hereditary optic neuropathy: evidence for preservation of melanopsin-expressing retinal ganglion cells. Invest Ophthalmol Vis Sci. Jul. 2, 2013;54(7):4471-4477.

Obara EA, et al. Loss of Melanopsin-Expressing Retinal Ganglion Cells in Patients With Diabetic Retinopathy. Invest Ophthalmol Vis Sci. Apr. 1, 2017;58(4):2187-2192.

Van de Kreeke JA, et al. Optical coherence tomography angiography in preclinical Alzheimer's disease. Br J Ophthalmol. May 2019.

O'Bryhim BE, et al. Association of Preclinical Alzheimer Disease With Optical Coherence Tomographic Angiography Findings. JAMA Ophthalmol. Nov. 1, 2018;136(11):1242-1248.

Doustar J, et al. Optical Coherence Tomography in Alzheimer's Disease and Other Neurodegenerative Diseases. Front Neurol. 2017;8:701.

De Rodez Benavent SA, et al. Fatigue and cognition: Pupillary responses to problem-solving in early multiple sclerosis patients. Brain Behav. May 17, 2017;7(7):e00717.

Caldito NG, et al. Brain and retinal atrophy in African-Americans versus Caucasian-Americans with multiple sclerosis: a longitudinal study. Brain. Nov. 1, 2018;141(11):3115-3129.

Frohman AR, et al. Multifocal visual evoked potentials are influenced by variable contrast stimulation in MS. Neurology. Aug. 21, 2012;79(8):797-801.

Yu, Jian, et al. "Relationship between retinal perfusion and retinal thickness in healthy subjects: an optical coherence tomography angiography study." Investigative ophthalmology & visual science 57.9 (2016): OCT204-OCT210.

International Application No. PCT/US21/25624 "International Search Report and Written Opinion" mailed Jul. 19, 2021, 8 pages.

Extended European Search Report for EP Application No. 21782071. 1, mailed Mar. 18, 2024, 10 pages.

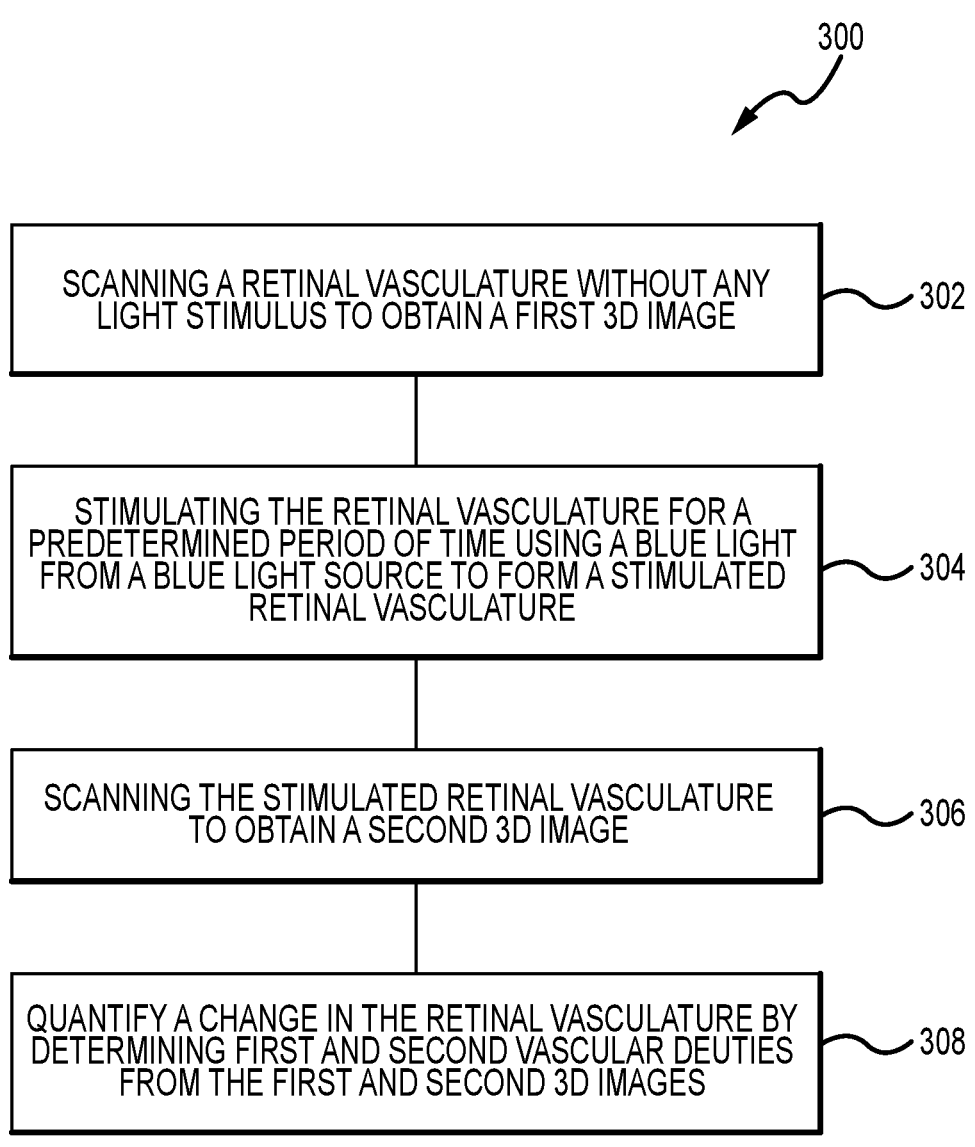

300

SCANNING A RETINAL VASCULATURE WITHOUT ANY LIGHT STIMULUS TO OBTAIN A FIRST 3D IMAGE ⌇302

STIMULATING THE RETINAL VASCULATURE FOR A PREDETERMINED PERIOD OF TIME USING A BLUE LIGHT FROM A BLUE LIGHT SOURCE TO FORM A STIMULATED RETINAL VASCULATURE ⌇304

SCANNING THE STIMULATED RETINAL VASCULATURE TO OBTAIN A SECOND 3D IMAGE ⌇306

QUANTIFY A CHANGE IN THE RETINAL VASCULATURE BY DETERMINING FIRST AND SECOND VASCULAR DEUTIES FROM THE FIRST AND SECOND 3D IMAGES ⌇308

FIG.3

SYSTEMS AND METHODS TO MEASURE RETINAL PERFUSION

CROSS REFERENCE TO RELATED APPLICATION APPLICATIONS

This application is a national stage application, filed under 35 U.S.C. § 371, of International Patent Application No. PCT/US2021/025624, filed Apr. 2, 2021, which claims the benefit of U.S. Provisional Patent Application No. 63/005,246, filed Apr. 4, 2020, the contents of which are incorporated by reference in their entireties.

BACKGROUND

Field

The present inventive concept is directed to systems and methods for performing a retinal angiogram. The systems and methods can be used to quantify retinal perfusion by measuring retinal vascular density. In particular, the systems and methods can be used to quantify retinal vascular density with selective stimulation of intrinsically photosensitive retinal ganglion cells (ipRGCs) through blue light, particularly in the choriocapillaris. The systems and methods can also be used to diagnose and follow progression in neurodegenerative conditions, associated sleep and mood disorders, and measuring metabolic reserve. In particular, the systems and methods can also be used for fatigue studies and investigating the melanopsin-mediated retinohypothalamic tract in multiple sclerosis.

Discussion of Related Art

Multiple sclerosis (MS) is the second most common cause of non-traumatic disability of young people and has been cited as the second most costly chronic disease behind congestive heart failure, with an annual average direct cost of $42 billion in the United States. With the increasing availability of treatment options for MS, relapses are becoming less frequent and there is increasing attention to progressive forms of the disease, where disability accumulates independent of relapses. Now that relapses are increasingly uncommon in multiple sclerosis, one of the major determinants of functional disability is the result of progressive rather than relapsing disease.

Neurodegeneration, or the progressive loss of structure and function in neurological disease, is a critical component of a number of disease processes, including but not limited to Alzheimer's Disease, Parkinson's Disease, Amyotrophic Lateral Sclerosis, Dementia with Lewy Bodies, Progressive Supranuclear Palsy, Multiple System Atrophy, the Spinocerebellar Ataxias, as well as Multiple Sclerosis. In Multiple Sclerosis, the neurodegeneration is often temporally independent of inflammation, necessitating the need for innovative biomarkers for disease.

The burden of neurodegenerative disease, even in disorders known primarily as inflammatory such as multiple sclerosis, is becoming a medical and economic burden. In disorders such as multiple sclerosis where structure and function can be localized, a biomarker of disease can help with therapeutic adventure. A better understanding of 1) the driving pathophysiology of vasculature in progressive retinal atrophy in multiple sclerosis, and 2) the impact of neurovascular coupling on patient symptomatology of fatigue and sleep may inform decisions on diagnosis and treatment for this neurodegenerative condition.

Optical Coherence Tomography (OCT) is a non-invasive technology that uses the reflectivity of light to measure the thickness of an object. OCT harnesses the different reflectivity of different materials including cells. OCT is a non-invasive, interferometric imaging modality that enables in vivo imaging of the retina in cross-section. OCT has been used to quantitatively evaluate retinal thickness and assess qualitative anatomic changes such as the presence or absence of many pathologic features, including intraregional and subretinal fluid. A three dimensional (3D) picture of the retina is often used in clinical medicine and research.

OCT-Angiography (OCT-A) uses similar OCT technology coupled with the mechanical properties of blood vessels, including movement of red blood cells, to develop an angiogram. OCT-A is an imaging technique based on OCT which allows for the visualization of functional blood vessels in the eye. The principle of OCT-A is to use the variation in OCT signal caused by moving particles, such as red blood cells (RBC), as the contrast mechanism for imaging vasculature.

To conceptualize this, imagine two OCT signals, one is backscattered from a static structural tissue and the other is backscattered from the moving RBCs in vessels. The signal from the static structural tissue remains steady, while the signal from the flowing blood changes over time due to the constant motion of the RBCs. To differentiate the moving particles from the static structural tissue, repeated scans are performed at the same location. Temporal changes of the OCT signal in subsequent scans caused by the moving particles generate the angiographic contrast, providing the opportunity to visualize the microvasculature. Notably, any moving particle may generate a motion contrast signal; however, the predominant movement in retinal tissue is from the RBCs.

Conventional systems suffer from various deficiencies. For instance, OCT-A is limited to producing a static image of blood vessels in retina, which has limited utility. As such, there is a need in the art to develop dynamic measures of functions, or an improved angiogram. In particular, there is a need in the art for systems and methods to non-invasively quantify retinal perfusion.

BRIEF SUMMARY

The following brief description is provided to indicate the nature of the subject matter disclosed herein. While certain aspects of the present inventive concept are described below, the summary is not intended to limit the scope of the present inventive concept. Embodiments of the present inventive concept provide systems and methods that satisfy the aforementioned needs of conventional systems, and can that can be used to non-invasively quantify retinal vascular response of the retina to visible spectrum light stimulation by measuring retinal vascular density. The systems and methods of the present inventive concept can be used to measure a response of intrinsically photosensitive retinal ganglion cells (ipRGCs) to blue light, particularly in the choriocapillaris. The systems and methods of the present inventive concept can be used to diagnose neurodegenerative conditions, associated sleep and mood disorders, ophthalmic disorders, and measure metabolic reserve. In particular, the systems and methods can also be used for fatigue studies and investigating the melanopsin-mediated retinohypothalamic tract in multiple sclerosis.

The aforementioned can be achieved in one aspect of the present inventive concept by providing a method of quantifying retinal blood flow or perfusion in an imaged retinal vasculature. The method may include measuring a vascular density of a baseline retinal vasculature to obtain a baseline vascular density. The method may further include stimulating the baseline retinal vasculature for a predetermined period of time using a blue light from a blue light source to form a blue light-stimulated retinal vasculature. The method may further include measuring a vascular density of the blue light-stimulated retinal vasculature to obtain a blue light-stimulated vascular density. The method may further include quantifying retinal perfusion in the retinal vasculature by quantifying a vascular density change between the baseline vascular density and the blue light-stimulated vascular density.

The retinal vasculature may be modulated by the intrinsically photosensitive retinal ganglion cells (ipRGCs). The retinal vasculature may include a choriocapillaris. The measuring of the vascular density of the baseline retinal vasculature and/or the measuring of the vascular density of the blue light-stimulated retinal vasculature may include scanning the baseline retinal vasculature and the blue light-stimulated retinal vasculature to obtain one or more 3D images of the baseline retinal vasculature and/or one or more 3D images of the blue light-stimulated retinal vasculature. The quantifying of the vascular density change may include comparing the one or more 3D images of the baseline retinal vasculature to the one or more 3D images of the blue light-stimulated retinal vasculature.

The vascular density of the baseline retinal vasculature and/or the vascular density of the blue light-stimulated retinal vasculature may be measured using optical coherence tomography angiography. The vascular density change stimulated by the blue light may be at least 6% relative to the baseline vascular density. The vascular density change stimulated by the blue light may be at least 8% relative to the baseline vascular density. The blue light source may be a light-emitting diode (LED) light source. The predetermined period of time may be at least 1 second. The blue light may be a wavelength of 440 nm to 495 nm. The blue light may have a wavelength of 463 nm. The baseline vascular density may include one or more measurements of the baseline retinal vasculature that has not been stimulated by light. The baseline retinal vasculature may be further stimulated using a red light from a red light source for a predetermined period of time. The blue light source and the red light source may be a same light source, for example, an LED light source with one or more LEDs. The red light may have a wavelength of 620-674 nm. The red light may have a wavelength of 622 nm.

The aforementioned can be achieved in another aspect of the present inventive concept by providing a method of diagnosing a neurodegenerative disease in a subject. The method may include measuring a vascular density of a baseline retinal vasculature to obtain a baseline vascular density. The method may further include stimulating the baseline retinal vasculature for a predetermined period of time using a blue light from a blue light source to form a blue light-stimulated retinal vasculature. The method may further include measuring a vascular density of the blue light-stimulated retinal vasculature to obtain a blue light-stimulated vascular density. The method may further include quantifying retinal perfusion in the retinal vasculature by quantifying a vascular density change between the baseline vascular density and the blue light-stimulated vascular density. The method may include comparing the retinal perfusion of the subject to one or more threshold values. The method may include determining the retinal perfusion is indicative of the neurodegenerative disease in the subject, if/when the retinal perfusion is a value above or below the one or more threshold values. The neurodegenerative disease may be Multiple Sclerosis, Alzheimer's Disease, Parkinson's Disease, or Dementia.

The aforementioned can be achieved in another aspect of the present inventive concept by providing a method of diagnosing a neurodegenerative disease in a subject. The method may include measuring a vascular density of a baseline retinal vasculature to obtain a baseline vascular density. The method may further include stimulating the baseline retinal vasculature for a predetermined period of time using a blue light from a blue light source to form a blue light-stimulated retinal vasculature. The method may further include measuring a vascular density of the blue light-stimulated retinal vasculature to obtain a blue light-stimulated vascular density. The method may further include quantifying retinal perfusion in the retinal vasculature by quantifying a vascular density change between the baseline vascular density and the blue light-stimulated vascular density. The method may include comparing the retinal perfusion of the subject to a training data set by using a machine learning algorithm to yield a comparison. The training data set may include retinal perfusion in positive individuals diagnosed with the neurodegenerative disease and/or retinal perfusion in negative individuals diagnosed as not having the neurodegenerative disease. The method may include classifying the retinal perfusion of the subject as positive or negative based on the comparison. The method may include diagnosing the neurodegenerative disease in the subject based on the classification. The neurodegenerative disease may be Multiple Sclerosis, Alzheimer's Disease, or Parkinson's Disease. Neurodegeneration may be attributed as the change in measured and/or calculated variables over a period of time.

The aforementioned can be achieved in another aspect of the present inventive concept by providing a system to quantify retinal vasculature changes. The system may include a first light source operable to emit a blue light on a retinal vasculature to stimulate the retinal vasculature. The system may include a second light source operable to emit an infrared light having a first portion and a second portion. The first portion may be emitted on the retinal vasculature to yield reflected light and/or backscattered light from the retinal vasculature. The second portion may be emitted to a reference system. The system may include a reference system operable to receive the second portion of the infrared light and yield a reference light. The system may include a coupler operable to receive the reflected light and/or the backscattered light from the retinal vasculature and the reference light from the reference system. The coupler may be operable to cause the reflected light and/or the backscattered light from the retinal vasculature and the reflected light from the reference system to interfere and form interference fringes. The system may include a detector operable to detect the interference fringes. The system may include a controller operable to initiate a stimulating process using the first light source, to initiate a scanning process of the retinal vasculature using the second light source, and/or to display one or more images based on the interference fringes.

The first light source may be one or more light-emitting diodes (LEDs). The second light source may be a laser source. The system may include a scanner operable to scan the first portion of the infrared light. The first portion of the infrared may be reflected light and/or backscattered light from the retinal vasculature. The controller may be configured to cause the first light source to emit the blue light for a predetermined period of time. The predetermined period of time may be at least one second. The retinal vasculature may be located in a choriocapillaris. The one or more images may be one or more three-dimensional (3D) images. It is foreseen that in addition to or in lieu any one or more of the one or more 3D images, the one or more images may be e one or more two-dimensional (2D) enface images of the retinal vasculature, without deviating from the scope of the present inventive concept.

Additional embodiments and features are set forth in part in the description that follows, and will become apparent to those skilled in the art upon examination of the specification or may be learned by the practice of the present inventive concept. A further understanding of the nature and advantages of the present inventive concept may be realized by reference to the remaining portions of the specification and the drawings, which forms a part of the present inventive concept.

BRIEF DESCRIPTION OF THE DRAWINGS

The description will be more fully understood with reference to the following figures and data graphs, which are presented as various embodiments of the present inventive concept and should not be construed as a complete recitation of the scope of the present inventive concept, wherein:

FIG. 3 is a flow chart illustrating steps to quantify retinal vasculature changes in accordance with an embodiment of the present inventive concept;

DETAILED DESCRIPTION

Figure 1:
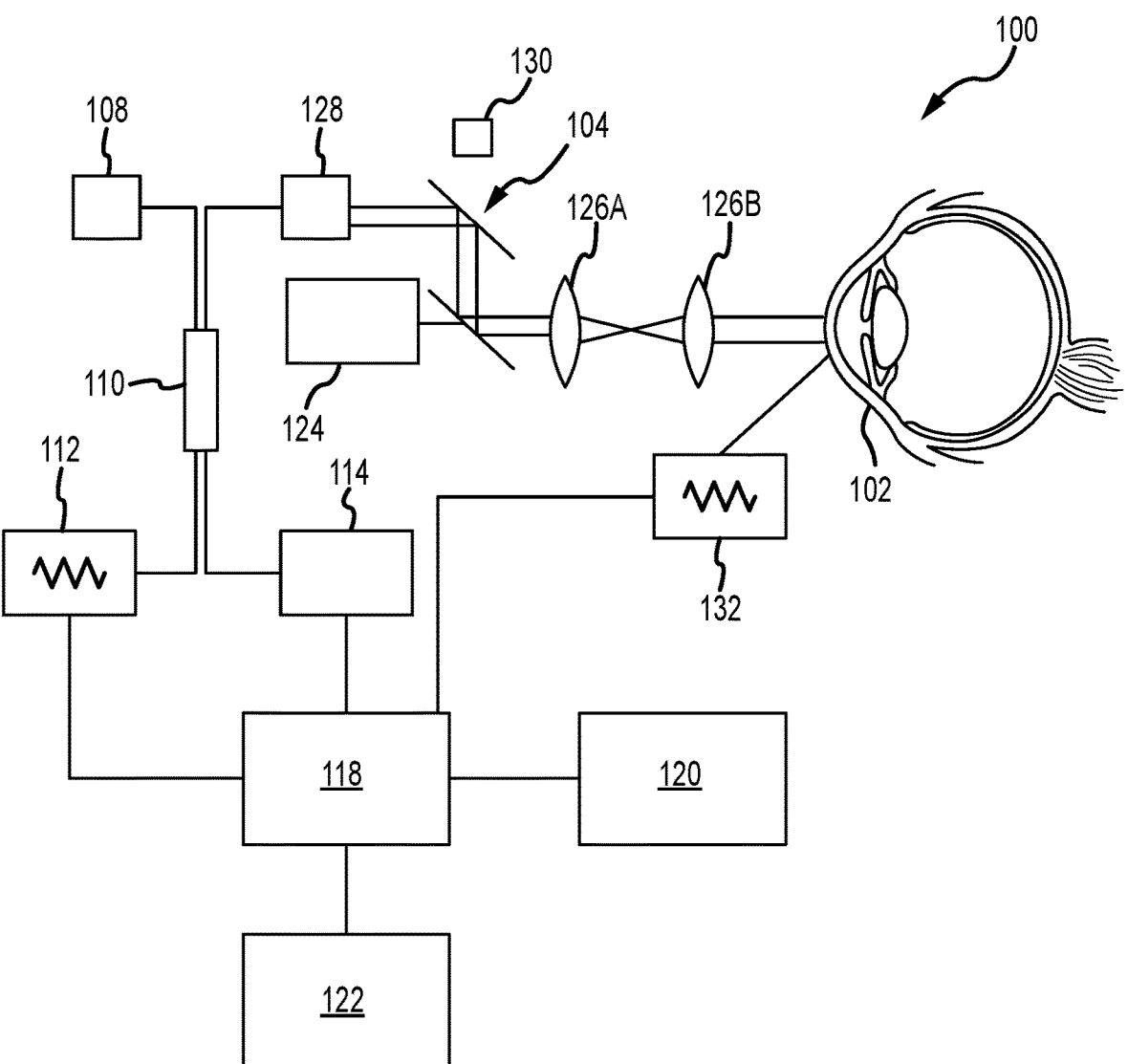
FIG. 1 is a system diagram including a first light source for stimulating a live human retina, and a second light source for scanning the live human retina to collect 3D images in accordance with an embodiment of the present inventive concept.

The present inventive concept may be understood by reference to the following detailed description, taken in conjunction with the drawings as described herein. It is noted that, for purposes of illustrative clarity, certain elements in various drawings may not be drawn to scale.

A retina is a light-sensitive tissue layer inside a human eye and includes many branches of small blood vessels or capillaries. The retina has a higher oxygen demand than the brain. Retinal perfusion is a process of delivering blood into the retina. A problem to be solved is to develop a way of quantifying retinal perfusion.

The present inventive concept provides a method to quantify retinal perfusion by using a unique light source that reliably and surprisingly creates a change in the capillary vessel density. The change in the capillary vessel density was surprisingly observed with a blue light in a particular layer of the retina (e.g. choriocapillaris). Therefore, a measurement of retinal perfusion with light stimulus is obtained non-invasively and under physiologic circumstances. The methodology can give insight into neurodegenerative conditions and can be used as a biomarker for metabolic reserve. The response of the choriocapillaris is indicative of a unique mechanism, possibly related to a unique biological phenomenon, or to disease.

One of the benefits of the present inventive concept is that the method is entirely non-invasive, and is conducted under physiologic, and therefore biologically relevant, conditions. This method provides benefits over conventional techniques, such as fluorescein angiography. While the fluorescein angiography provides similar information, it is not reliably quantifiable, is more expensive, and carries the risk of serious reactions to the intravenously administered dye. The fluorescein angiogram involves the use of an injectable dye. Intravenous dye injection is time consuming and can have adverse side effects, such as anaphylaxis and death. From a physics perspective, the dye-based method utilizes the phenomenon of fluorescence. For fluorescein angiography, the fluorescence corresponds to an excitation wavelength of blue (around 470 nm) and an emission wavelength near yellow (520 nm).

While standard optical coherence tomography angiography informs on vessel density and other static metrics, the system and method of the present inventive concept allow one to obtain a signal that is measurably different disseminated in time, and therefore an ability to measure retinal perfusion.

Method of Quantifying Retinal Perfusion

The present inventive concept provides a method of measuring retinal perfusion by measuring changes in retinal vascular density based on a very clinically useful condition in neuro-ophthalmology: light. The present inventive concept provides methods to quantify retinal perfusion, and systems operable to perform the quantification. The retinal perfusion can be quantitatively determined by quantifying vascular densities. The method includes the use of a blue light source, which may be one or more light emitting diodes, to stimulate cells. The cells may be located in the retinal vasculature. In particular, the cells of the retinal vasculature may be intrinsically photosensitive, which may respond to blue light. The cells may be the intrinsically photosensitive retinal ganglion cells (ipRGCs). In particular, the ipRGCs being stimulated may be located in the ganglion cell layer.

The blue light may stimulate a change retinal vascular density in the retinal vasculature as compared to a baseline vascular density, and the change may be used to quantify the amount of blood flow. Retinal blood flow may be calculated by measuring the vascular density of a predetermined imaged retina and subtracting it from a similarly calculated unstimulated retinal image. Retinal perfusion may be calculated by multiplying retinal blood flow by a predetermined retinal density constant. The blue light may have a wavelength of about 440-495, 450-480, or 460-470 nm. In particular, the blue light may have a wavelength of 461, 462, 463, 464, or 465 nm, preferably 463 nm. The blue light may be used to stimulate the retinal vasculature for a predetermined time. The time may be 1 second or at least 1 second. The blue light stimulus was effective in resulting in significant change from the baseline vascular density.

The baseline vascular density may be measured in retinal vasculature that has not been stimulated by light. One or more measurements of vascular density in the absence of light stimulus may be used to determine the baseline vascular density. The vascular density may also include measuring vascular density of the retinal vasculature in response to a red light source, which may be for a predetermined period of time. The red light may have a wavelength of 620-674 nm, and particularly 622 nm. However, the red light stimulus was not as effective as the blue light stimulus in resulting in significant change from the baseline vascular density.

The blue light-stimulated vascular density may be at least, 5, 6, 7, 8, 9, 10, 11, 12, 13, 14, or 15% higher than the baseline vascular density. In particular, the blue light-stimulated vascular density may be 6.5% or 8% higher than the baseline vascular density.

Vascular densities may be quantified from 3D images obtained by scanning the retinal vasculature. In particular, optical coherence tomography may be used.

Methods of Diagnosis

The amount of retinal perfusion may be used to diagnose a neurodegenerative disorder in a subject, such as Multiple Sclerosis (MS), Alzheimer's disease (AD), or Parkinson's disease, glaucoma, diabetic retinopathy, macular edema, macular degeneration, uveitis, ischemic optic neuropathies, central serous chorioretinopathy, macular telangiectasia, neovascular membranes, choroidal neovascularization, stiff person syndrome, encephalitis, or an associated fatigue, sleep and/or mood disorder. Accordingly, provided herein are methods of making such diagnoses by providing the amount of retinal perfusion of a subject as described herein. The subject may be a mammal, and may be a human. The amount of retinal perfusion may also be used as a biomarker for metabolic reserve or metabolism.

A difference in retinal perfusion in the subject as compared to one or more threshold levels may be indicative of the neurodegenerative disorder or associated fatigue, sleep, or mood disorder. In particular, a reduced or increased amount of retinal perfusion as compared to the threshold may be indicative. The method of diagnosis may include providing a quantity of retinal perfusion of the subject, and comparing the quantity to one or more threshold values. A difference between the quantity of retinal perfusion as compared the one or more threshold values may be indicative of the neurological disorder, ophthalmological disorder, or associated fatigue, sleep, or mood disorder. The quantity of retinal perfusion may be lower in a subject having the neurodegenerative disorder or associated fatigue, sleep, or mood disorder, as compared to the one or more threshold values.

The quantity of retinal perfusion may also be used in a machine learning method to diagnose the subject. The machine learning method may use a controller and a memory device with a machine learning algorithm and a training data set stored therein. The training data set may include amounts of retinal perfusion in subjects diagnosed as having or not having the neurodegenerative disorder or associated fatigue, sleep, or mood disorder. In particular, the machine learning method may include providing the training data set to which the quantity of retinal perfusion in the subject is compared. The training data set may include one or more quantities of retinal perfusion in one or more individuals who have been diagnosed as being positive for the neurodegenerative disorder or associated fatigue, sleep, or mood disorder. The training data set may also include one or more quantities of retinal perfusion in one or more individuals who have been diagnosed as not having the neurodegenerative disorder or associated fatigue, sleep, or mood disorder. Based on the comparison between the subject's quantity of retinal perfusion and the training data set, the subject may be classified as having or not having the neurodegenerative disorder or associated fatigue, sleep, or mood disorder, and the subject may be diagnosed accordingly. The training data set may be initially formed by human-entered data and/or by a machine-learning approach that determines based on historical, human-entered data whether the training data set should be modified based on new data.

FIG. 1 is a system diagram including a first light source for stimulating a live human retina, and a second light source for scanning the live human retina to collect 3D images in accordance with an embodiment of the present inventive concept. A system 100 includes a first light source 132, which can emit light to stimulate the retinal vasculature of a human eye. In some variations, the first light source 132 a light-emitting diode (LED), emitting a visible light, such as a blue light and/or a red light, among others.

The system 100 also includes a controller 118 with a processor, which can control the first light source 132 to stimulate the retinal vasculature structure for a predetermined time. For example, the controller 118 initiates the light stimulus and ends the light stimulus after the predetermined time. The stimulus time is for at least 0.9 seconds. In some variations, the stimulus time is at least 1 second. Note that a shorter stimulus time less than 0.9 seconds may be inadequate to stimulate noticeable flow increase in blood vessel. However, if the stimulus time were too long, the effect of light stimulation on the retinal vasculature may disappear. Another light stimulus would be required. There is a time window for scanning the retinal vasculature.

The system 100 also includes a second light source 112 operable to emit an infrared (IR) light. In some variations, the wavelength for the second light source 112 may vary from 700 nm to 1350 nm. In a particular embodiment, the second light source 112 may include a laser source operable to emit a laser at 1350 nm with a 100-nm tuning range. The laser may have a tuning cycle having a repetition rate of 100 kHz and a duty cycle of 50%. In another embodiment, the wavelength may be 840 nm with a bandwidth of 45 nm. It is foreseen that the second light source may be a superluminescent diode or a swept source laser without deviating from the scope of the present inventive concept. It also foreseen that the source frequency may be fixed or tunable without deviating from the scope of the present inventive concept.

The system 100 also includes a scanner 104 for scanning the light toward an eye 102. The scanner 104 includes two reflecting mirrors (e.g. galvano mirrors) and a driving device 130 for adjusting the reflection angles of the reflecting mirrors. For the scanning, the average output power of the second light source is 1.2 mW, consistent with safe ocular exposure limits set by the American National Standards Institute (ANSI). The system 100 has a resolution of 1-5 μm, and an imaging range of 1 μm×1 μm to 12 mm×12 mm in the eye 102.

The system 100 functions by comparing sequential scans of the same cross-section of a retina of the eye 102. Many cross-sections can be scanned over time to get a 3D view of the retina of the eye 102. Low-coherence interferometry is used to perform each scan. The system 100 is operable to emit an infrared light onto the retina of the eye 102 and measures interference patterns of the infrared light that is reflected and/or backscattered from the retina of the eye 102. Areas of change between each sequential scan can then be distinguished as sites of blood flow. The scans are then added together to yield a 3D image of the retina of the eye 102. The resulting image provides structural and functional information of the retinal layers and the vasculature found at each layer of the retina of the eye 102.

The system 100 also includes a reference system 108 and a coupler 110. The light returning from the reference system 108 and the reflected light and/or backscattered light from the patient object (e.g. the eye 102) interfere at a coupler 110 to generate interference fringes. The interference fringes are then digitized by a high speed digitizer or analog-to-digital (A/D) converter (not illustrated). This analog-to-digital signal acquisition is driven by an optical clock output in communication with the second light source 112.

In some variations, the system 100 of the present inventive concept can split light from the second light source 112 into a first portion of light (e.g. 70%) and a second portion of light (e.g. 30%). The first portion of light proceeds to reach a patient interface (e.g. the eye 102). The second portion of light (e.g. 30%) reaches to the reference system 108.

In some variations, the coupler 110 may be a 50/50 coupler in which 50% reflected light and/or backscattered light from the patient and 50% reflected light from the reference system 108 interfere, thereby resulting in interference. This interference provides phase information for use in producing 3D images.

The system 100 also includes a front optical system 124 for viewing the eye 102. The system 100 further includes a detector 114 operable to detect the interference fringes generated by the coupler 110. In some variations, the detector 114 is operable to detect digitized signals of the interference fringes using an analog-to-digital converter in communication with the detector 114.

Referring to the controller 118 again, the controller 118 connects to the first light source 132 and controls the first light source 132 to stimulate the retinal vasculature structure, as described above. The controller 118 also connects to the detector 114, and controls data collection from the detector 114. The controller 118 also connects to the second light source 112, and controls the output of the second light source 112. The controller 118 also controls the scanning of the scanner 104 and the driving device 130.

The controller 118 also includes a memory device 122 coupled to the controller for storing data and storing algorithms or instructions for data acquisition. The memory device 122 also stores a data analysis software for analyzing the collected data to create 3D images and stores the results from the data analysis.

The first portion of light is coupled to the scanner 104. A focused spot diameter (e.g. 1-18 μm) is estimated on the retinal plane based on an eye model.

The system 100 further includes a data analysis software for analyzing the collected data to create 3D images. The system 100 is capable of providing 3D images of the retinal vasculature, which includes five anatomic layers, i.e. the superficial vascular complex, the deep vascular complex, the avascular zone, the choriocapillaris, and the choroid. Combinations of the vascular zones, or subsections thereof, can be used for finite analysis.

The system 100 also includes a display 120 coupled to the controller 118 for displaying images and results from the data analysis, such as vascular densities.

In some embodiments, the system 100 is an integrated system.

Figure 2:
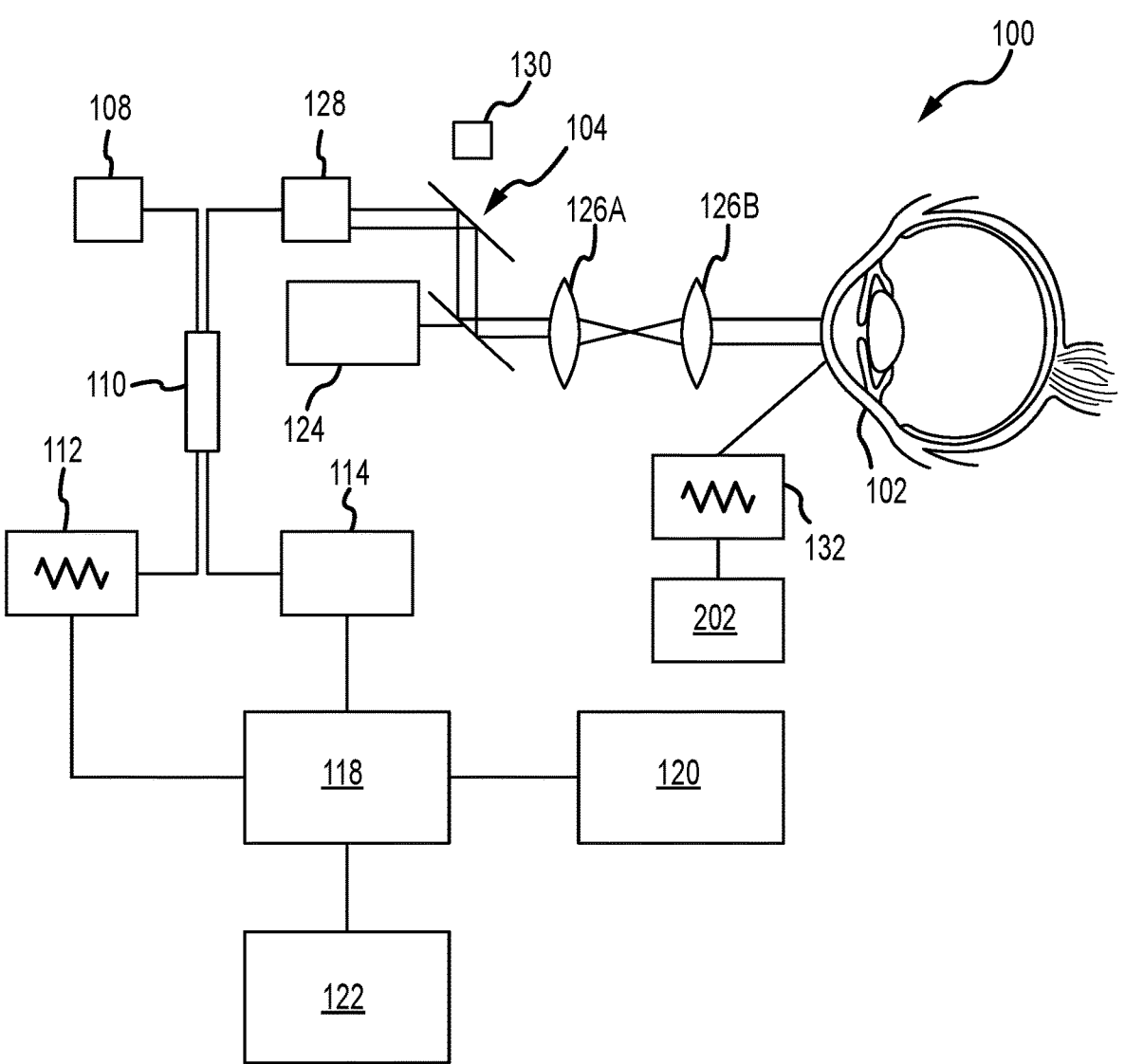
FIG. 2 illustrates a simplified system diagram including a separate switch controller for a first light source for stimulating a live human retina and a controller for a second light source for scanning the live human retina to collect 3D images in accordance with an embodiment of the present inventive concept.

FIG. 2 illustrates a simplified system diagram including a separate switch controller for a first light source for stimulating a live human retina and a controller for a second light source for scanning the live human retina to collect 3D images in accordance with an embodiment of the present inventive concept. As shown in FIG. 2, the first light source 132 may be controlled by a switch controller 202 to stimulate the retinal vasculature. The switch controller 202 may be separated from the controller 118 for scanning the patient object, e.g., the eye 102.

FIG. 3 is a flow chart illustrating the steps of quantifying retinal vasculature changes in accordance with an embodiment of the present inventive concept. A method 300 of the present inventive concept uses the system 100, such as illustrated in FIG. 1 or FIG. 2, to quantify retinal vasculature changes with light stimulation. The method 300 includes scanning a retinal vasculature without any light stimulus to obtain a first 3D image at operation 302. The method 300 also includes stimulating the retinal vasculature for a predetermined period of time using a blue light from a blue light source to form a stimulated retinal vasculature at operation 304.

In some variations, the blue light has a wavelength ranging from 380 nm to 495 nm.

In some variations, the stimulus time for the blue light ranges from 1 second to 600 seconds.

In some variations, the stimulus time for the blue light is equal to or greater than 1 second. In some variations, the stimulus time for the blue light is equal to or greater than 10 seconds. In some variations, the stimulus time for the blue light is equal to or greater than 100 seconds. In some variations, the stimulus time for the blue light is equal to or greater than 200 seconds. In some variations, the stimulus time for the blue light is equal to or greater than 300 seconds. In some variations, the stimulus time for the blue light is equal to or greater than 400 seconds. In some variations, the stimulus time for the blue light is equal to or greater than 500 seconds.

In some variations, the stimulus time for the blue light is less than or equal to 10 seconds. In some variations, the stimulus time for the blue light is less than or equal to 100 seconds. In some variations, the stimulus time for the blue light is less than or equal to 200 seconds. In some variations, the stimulus time for the blue light is less than or equal to 300 seconds. In some variations, the stimulus time for the blue light is less than or equal to 4000 seconds. In some variations, the stimulus time for the blue light is less than or equal to 500 seconds. In some variations, the stimulus time for the blue light is less than or equal to 600 seconds.

The method 300 also includes scanning the stimulated retinal vasculature to obtain a second 3D image at operation 306. The method 300 further includes quantifying a change in the retinal vasculature by determining first and second vascular densities from the respective first and second 3D images at operation 308.

Figure 4:
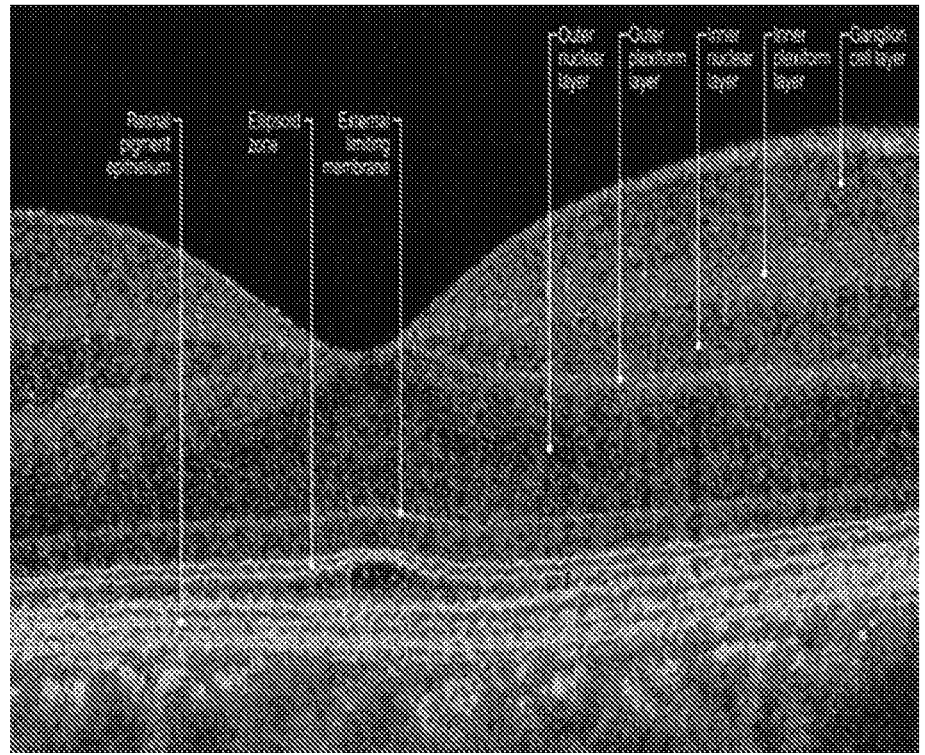
FIG. 4 illustrates a 3D image of a retina by using an OCT in accordance with an embodiment of the present inventive concept.

FIG. 4 illustrates a 3D image of a retina by using an OCT in accordance with an embodiment of the present inventive concept. As shown in FIG. 4, the 3D image of the retina revealed a very high spatial resolution, showing multiple layers including a ganglion cell layer, an inner plexiform layer, an inner nuclear layer, an outer plexiform layer, an outer nuclear layer, an external limiting member, an ellipsoid zone, and a retinal pigment epithelium layer, as indicated by labels.

Figure 5:
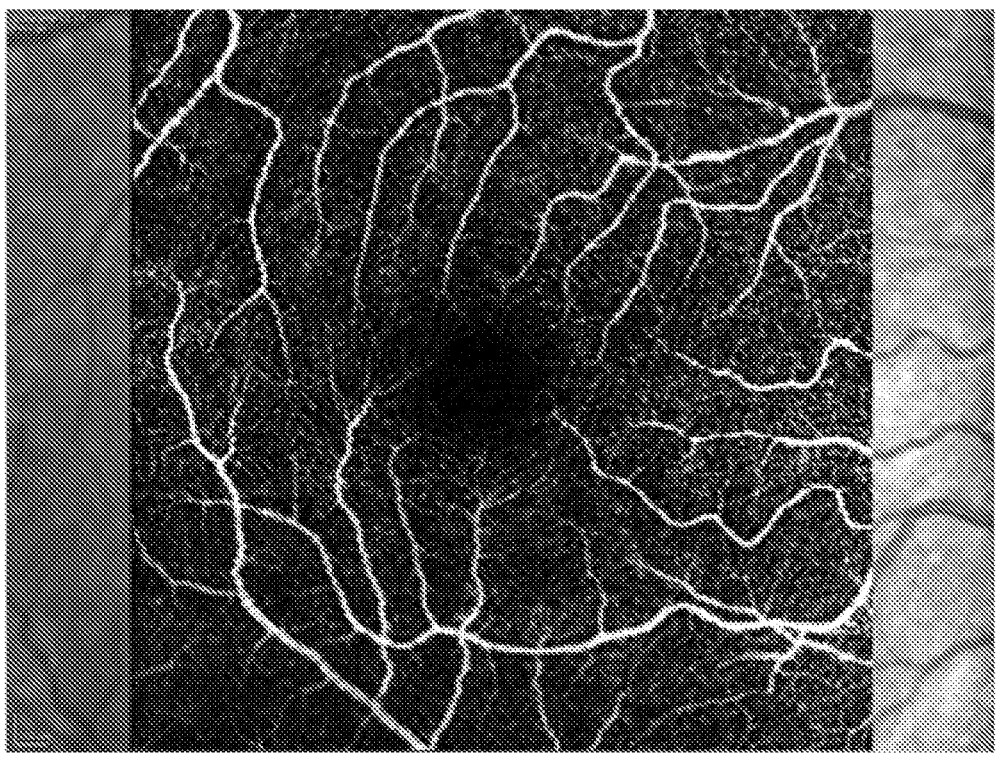
FIG. 5 illustrates a 3D image of a retinal vasculature by using an OCT-A in accordance with an embodiment of the present inventive concept.

FIG. 5 illustrates a 3D image of a retinal vasculature by using an OCT-A in accordance with an embodiment of the present inventive concept. As shown, small blood vessels or capillaries (light color) were visible. Vascular density can be obtained based upon the 3D image.

EXAMPLES

The present technology is further illustrated by the following Examples, which should not be construed as limiting in any way. The following examples demonstrate that light stimulation for the retinal vasculature was dependent upon the wavelength. For example, a blue light stimulus works better than a red light stimulus. Also, a particular layer of the retinal vasculature (e.g. choriocapillaris) was more sensitive to light stimulus than other layers of the retinal vasculature (e.g. superficial vascular plexus).

Example 1

By using the system, such as illustrated in FIG. 1 or FIG. 2, 3D, images were obtained for the same spot on superficial vascular plexus by several scans in sequential time. A first 3D image was obtained without any light stimulus from the first light source 132 to establish a first baseline. A second 3D image was obtained without any light stimulus from the first light source 132 to establish a second baseline. A third 3D image was obtained with a red light stimulus from the first light source 132. A fourth 3D image was obtained with a blue light stimulus from the first light source 132.

The first light source 132 was an LED emitting blue light or an LED emitting red light. The LED emitted an intensity of 180 lux. In some variations, the intensity may vary between 0.01 lux and 1000 lux. In some variations, the intensity may be equal to or greater than 0.1 lux. In some variations, the intensity may be equal to or greater than 1 lux. In some variations, the intensity may be equal to or greater than 10 lux. In some variations, the intensity may be equal to or greater than 100 lux. In some variations, the intensity may be less than or equal to 1000 lux. In some variations, the intensity may be less than or equal to 100 lux. In some variations, the intensity may be less than or equal to 10 lux. In some variations, the intensity may be less than or equal to 1 lux. In some variations, the intensity may be less than or equal to 0.1 lux. The stimulus time for each of the third and fourth 3D images was about 1 second. In some variations, the stimulus time may be 0.9 seconds. In some variations, the stimulus time may be 0.95 seconds. Note that a shorter stimulus time of less than 1 second was inadequate to stimulate noticeable flow increase in blood vessel. These 3D images were shown on the display 120.

Figure 6A:
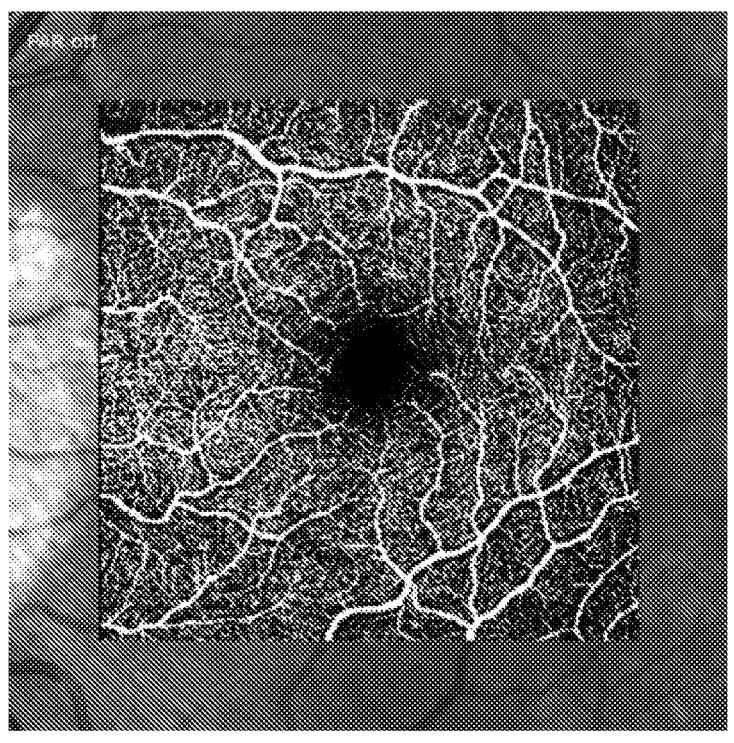
FIG. 6A illustrates a first 3D image from a first scan for superficial vascular plexus without any light stimulus in accordance with an embodiment of the present inventive concept.
Figure 6B:
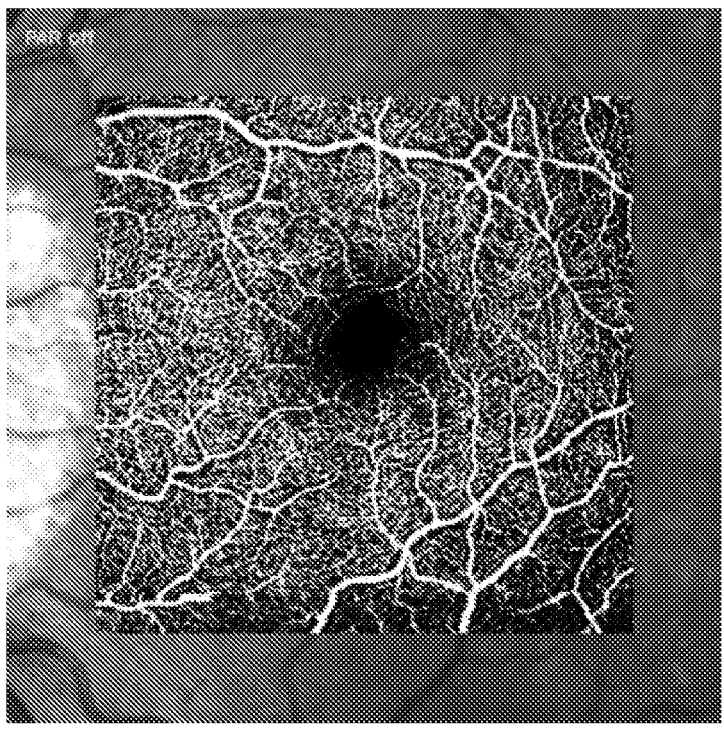
FIG. 6B illustrates a second 3D image from a second for superficial vascular plexus without any light stimulus in accordance with an embodiment of the present inventive concept.
Figure 6C:
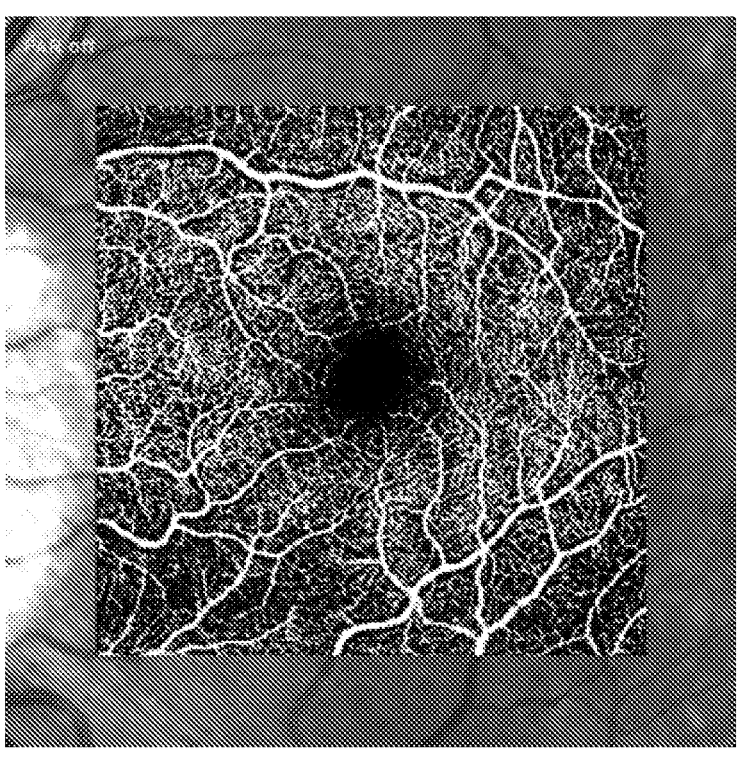
FIG. 6C illustrates a 3D image from a scan for superficial vascular plexus with a red light stimulus in accordance with an embodiment of the present inventive concept.
Figure 6D:
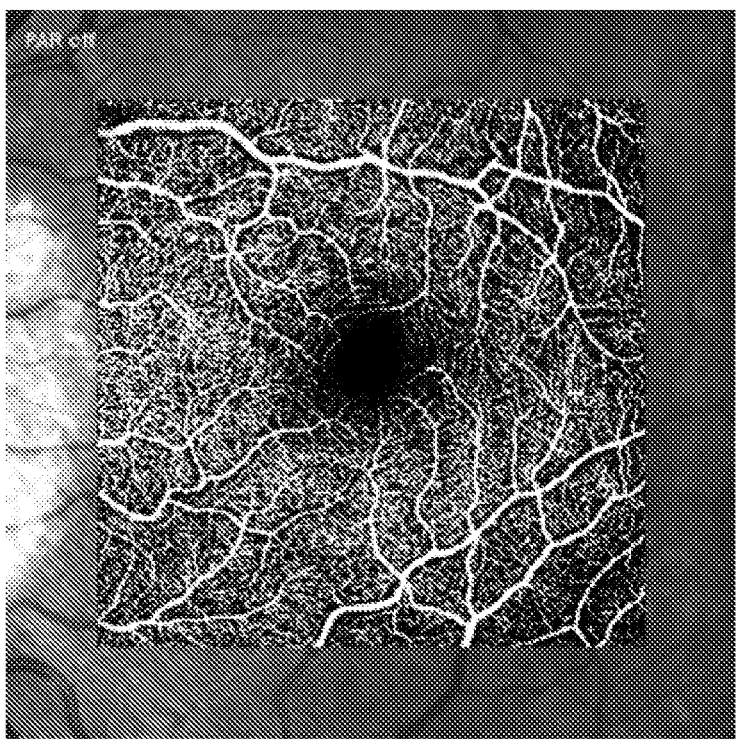
FIG. 6D illustrates a 3D image from a scan for superficial vascular plexus with a blue light stimulus in accordance with an embodiment of the present inventive concept.

FIG. 6A illustrates a first 3D image from a first scan for superficial vascular plexus without any light stimulus in accordance with an embodiment of the present inventive concept. FIG. 6B illustrates a second 3D image from a second for superficial vascular plexus without any light stimulus in accordance with an embodiment of the present inventive concept. FIG. 6C illustrates a 3D image from a scan for superficial vascular plexus with a red light stimulus in accordance with an embodiment of the present inventive concept. FIG. 6D illustrates a 3D image from a scan for superficial vascular plexus with a blue light stimulus in accordance with an embodiment of the present inventive concept. As shown in these images, the light color areas were blood vessels. The dark areas were absent of blood vessels.

Based upon the 3D images shown in FIGS. 6A-6D, vascular densities were determined by using the data analysis software stored in memory device 122. In this manner, the software of the present inventive concept provides the data analysis of the 3D images to determine the vascular densities. Vascular density was determined by the amount of vessels for the same image area and reported in percent. Table 1 lists vascular densities for superficial vascular plexus. As shown in Table 1, a first baseline without any light stimulus was determined by a first scan image for superficial vascular plexus. The first baseline had a vascular density of 52.0%. A second baseline without any light stimulus was determined by a second scan image. The second baseline had a vascular density of 57.5%, which was inconsistent with the first baseline for superficial vascular plexus. The error in vascular density for the baselines was quite large, e.g. 5.5%, for superficial vascular plexus.

TABLE 1

| Vascular Densities for Superficial Vascular Plexus | |
| --- | --- |
| Condition | Vascular Density (%) |
| 1st Baseline without light stimulus | 52.0 |
| 2nd Baseline without light stimulus | 57.5 |
| Red light stimulus | 53.2 |
| Blue light stimulus | 57.0 |

The red light (wavelength of 622 nm) stimulus resulted in a vascular density of 53.2%, which was between the first and second baselines (e.g. 52.0% and 57.5%), and was within the error of the baseline values. In contrast, the blue light (e.g. a wavelength of 463 nm) stimulus resulted in a vascular density of 57.0%, which was close to the second baseline value (e.g. 57.5%). As shown, the vascular density was inaccurate for superficial vascular plexus. Also, the light stimulus, regardless of red light or blue light, the vascular density did not appear to increase. As the vascular density post stimulation was within the bounds of the baseline scans, there did not appear to be a significant influence of this light stimulation protocol of the retinal vasculature.

In some variations, the blue light has a wavelength ranging from 380 nm to 495 nm.

In some variations, the blue light has a wavelength equal to or greater than 380 nm. In some variations, the blue light has a wavelength equal to or greater than 400 nm. In some variations, the blue light has a wavelength equal to or greater than 420 nm. In some variations, the blue light has a wavelength equal to or greater than 440 nm. In some variations, the blue light has a wavelength equal to or greater than 460 nm. In some variations, the blue light has a wavelength equal to or greater than 480 nm.

In some variations, the blue light has a wavelength less than or equal to 490 nm. In some variations, the blue light has a wavelength less than or equal to 480 nm. In some variations, the blue light has a wavelength less than or equal to 460 nm. In some variations, the blue light has a wavelength less than or equal to 440 nm. In some variations, the blue light has a wavelength less than or equal to 420 nm. In some variations, the blue light has a wavelength less than or equal to 400 nm.

Example 2

By using the system 100, such as in FIG. 1 or FIG. 2, 3D images were obtained for the same spot on choriocapillaris by several scans in sequential time. A first 3D image was obtained without any light stimulus from the first light source 132 to establish a first baseline. A second 3D image was obtained without any light stimulus from the first light source 132 to establish a second baseline. A third 3D image was obtained with a red light stimulus from the first light source 132. A fourth 3D image was obtained with a blue light stimulus from the first light source 132. It is foreseen that the red light source may be a separate light source, e.g., an LED, or the first light source 132 may be configured to emit red light as well as blue light, without deviating from the scope of the present inventive concept.

The first light source 132 was an LED emitting blue light or an LED emitting red light. The LED was bright. In some variations, the intensity may vary between 0.01 lux and 1000 lux. In some variations, the intensity may be equal to or greater than 0.1 lux. In some variations, the intensity may be equal to or greater than 1 lux. In some variations, the intensity may be equal to or greater than 10 lux. In some variations, the intensity may be equal to or greater than 100 lux. In some variations, the intensity may be less than or equal to 1000 lux. In some variations, the intensity may be less than or equal to 100 lux. In some variations, the intensity may be less than or equal to 10 lux. In some variations, the intensity may be less than or equal to 1 lux. In some variations, the intensity may be less than or equal to 0.1 lux. The stimulus time for each of the third and fourth 3D images was 1 second. These 3D images were shown on the display 120.

Figure 7A:
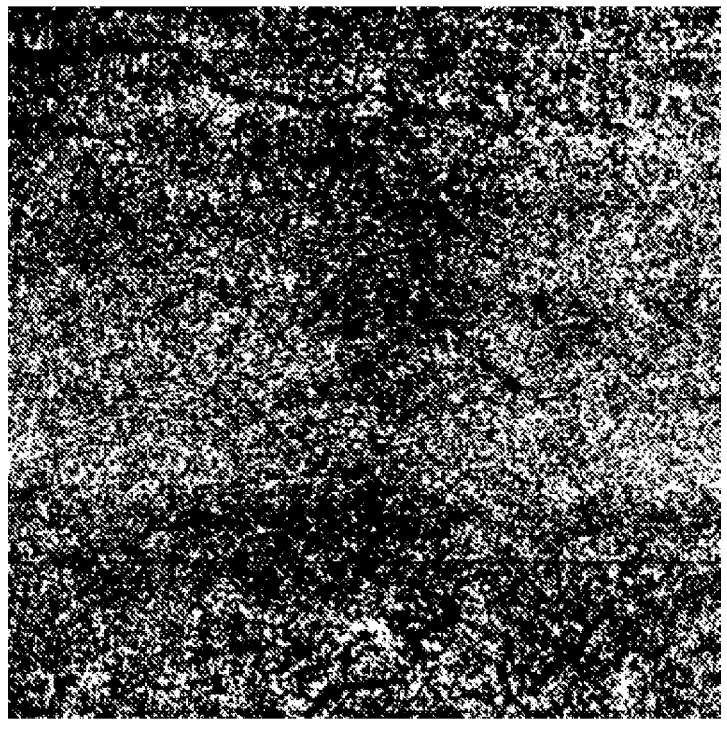
FIG. 7A illustrates a first 3D image from a first scan for choriocapillaris without any light stimulus in accordance with an embodiment of the present inventive concept.
Figure 7B:
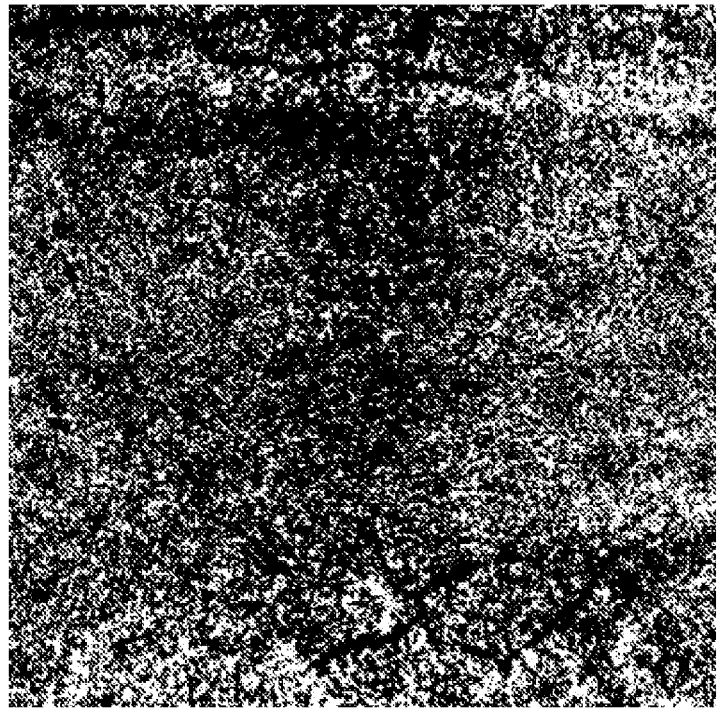
FIG. 7B illustrates a second 3D image from a second for choriocapillaris without any light stimulus in accordance with an embodiment of the present inventive concept.
Figure 7C:
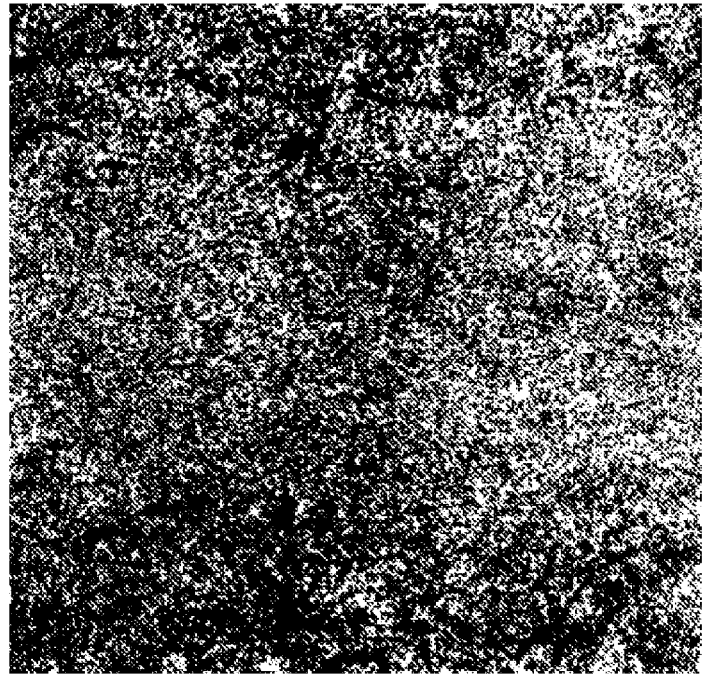
FIG. 7C illustrates a 3D image from a scan for choriocapillaris with a red light stimulus in accordance with an embodiment of the present inventive concept.
Figure 7D:
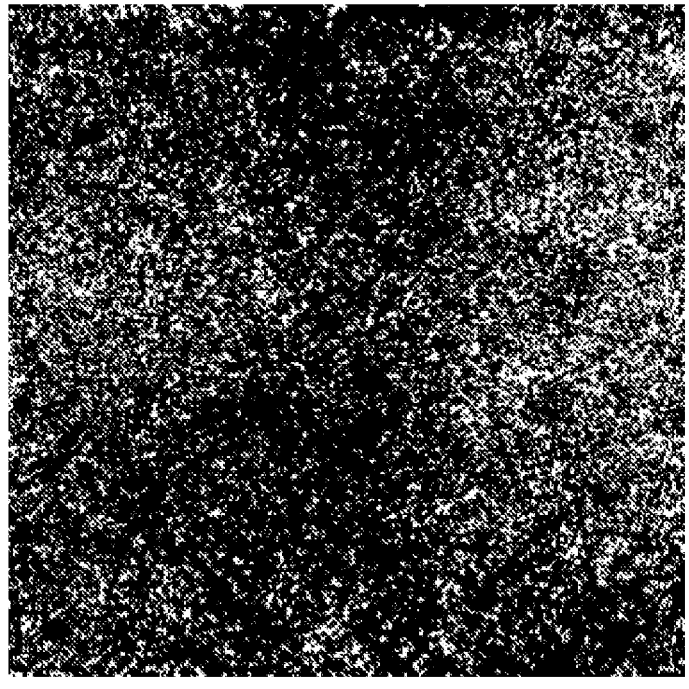
FIG. 7D illustrates a 3D image from a scan for choriocapillaris with a blue light stimulus in accordance with an embodiment of the present inventive concept.

FIG. 7A illustrates a first 3D image from a first scan for choriocapillaris without any light stimulus in accordance with an embodiment of the present inventive concept. FIG. 7B illustrates a second 3D image from a second for choriocapillaris without any light stimulus in accordance with an embodiment of the present inventive concept. FIG. 7C illustrates a 3D image from a scan for choriocapillaris with a red light stimulus in accordance with an embodiment of the present inventive concept. FIG. 7D illustrates a 3D image from a scan for choriocapillaris with a blue light stimulus in accordance with an embodiment of the present inventive concept. As shown in these images, the light color areas were blood vessels. The dark areas were absent of blood vessels.

Based upon the 3D images shown in FIGS. 7A-7D, vascular densities were determined by using the data analysis software stored in memory device 122. In this manner, the software of the present inventive concept provides the data analysis of the 3D images to determine the vascular densities. Vascular density was determined by the amount of vessels for the same image area and reported in percent.

Table 2 lists the vascular densities for choriocapillaris. As shown in Table 2, a first baseline without any light stimulus was determined by a first scan image for choriocapillaris. The first baseline had a vascular density of 67.3%. A second baseline without any light stimulus was determined by a second scan image. The second baseline had a vascular density of 67.7%, which was consistent with the first baseline for choriocapillaris. As such, the vascular density was reproducible for choriocapillaris.

TABLE 2

| Vascular Densities for Choriocapillaris | |
| --- | --- |
| Condition | Vascular Density (%) |
| 1st Baseline without light stimulus | 67.3 |
| 2nd Baseline without light stimulus | 67.7 |
| Red light stimulus | 63.2 |
| Blue light stimulus | 76.3 |

A red light (a wavelength of 622 nm) stimulus resulted in a decreased vascular density of 63.2% compared to the first and second baselines. The change resulted from the red light stimulation was about 3%, which was less than an error of 6% from the measurement.

In contrast, a blue light stimulus with a wavelength of 463 nm resulted in an increased vascular density of 76.3% compared to the first and second baselines. The change of the vascular density stimulated by the blue light was about 9% for choriocapillaris. The increased vascular density indicated an increased flow in blood vessels. The blue light stimulus significantly increased the vascular density such that choriocapillaris was identified as the localized retinal structure for disease associations.

Applications

The diseases that may be affected by the methods and systems of the present inventive concept include multiple sclerosis, Alzheimer disease, Parkinson disease, Dementia, neurodegenerative disorders, sleep disorders, glaucoma, macular degeneration, and other retinal disorders, among others, including those described herein.

Fatigue Study

Fatigue affects up to 92% of patients with multiple sclerosis (MS), and is strongly linked with poor quality of life, lack of employment, and impaired individual psychological wellbeing. While particularly prevalent and often multifactorial, fatigue is not consistently associated with disability or disease activity in MS (e.g. Salter 2019). While most symptoms experienced by MS patients have clear neurological structural localization, a focal lesion causing fatigue has not been identified.

Pathology along the visual system is nearly universal in MS; however, its contribution to fatigue and mood disorders has yet to be fully elucidated. A link was found between this pathology and the melanopsin-mediated retinohypothalamic tract. Using a specific wavelength light in multichromatic pupillography to precisely stimulate the intrinsically photosensitive retinal ganglion cells in vivo was found to activate the hypothalamus which is critical to the phase-locking circadian rhythms that initiate wake and sleep onset (e.g. Meltzer 2017).

Data suggested that the retinohypothalamic tract's function correlated with retinal anatomy. This was quantified by Optical Coherence Tomography (OCT) which measures the thickness of the retinal nerve fiber layer. Yet, this fixed measure of anatomy does not give a dynamic measure of function and as such the association was not perfect.

Developing a functional measure of retinal response to light may provide a mechanism for determining if visual pathway dysfunction may help explain fatigue mediated by changes to the hypothalamic pathway.

The system 100 can quantify the retinal vasculature change with light stimulus, which had associations with patient centered outcomes focused on retinohypothalamic tract determinants. Localizing retinal structure and function may improve these disease associations.

The methods and systems of the present inventive concept can be leveraged as a closed-loop biomarker for neurological function that captures axon, myelin, and vascular functions. For example, the methods and system of the present inventive concept can be used to understand how MS-mediated dysfunction of the melanopsin-mediated retinohypothalamic tract relates to hypothalamic dysfunction. The MS-mediated dysfunction of the melanopsin-mediated retinohypothalamic tract may be used as a biomarker for function in MS. Melanopsin-mediated retinohypothalamic tract dysfunction may positively correlate with the severity of patient-centered outcomes of fatigue, sleep, and mood when controlled for covariates.

The system and method of the present inventive concept can be used for investigation of the melanopsin-mediated retinohypothalamic tract in MS includes a cohort of patients diagnosed with MS. The investigations may elucidate the pathophysiology of fatigue in MS, and provide further evidence to understand progressive MS. Melanopsin-mediated retinohypothalamic tract dysfunction can provide a very translatable system for the individual patient, and can provide both a diagnostic and therapeutic biomarker for future trials in MS.

Multiple Sclerosis (MS) Study

MS is a debilitating demyelinating disease of the central nervous system affecting predominantly younger people. While there are many symptoms localizable to discrete CNS lesions (e.g. weakness, vision loss, sensory deficits), there are numerous debilitating symptoms that are not easily related to discrete lesions (e.g. fatigue and sleep disturbances). Often, the fatigue and sleep disturbances of MS cause more disability than lesions to motor or sensory tracts. Pathologically, MS is associated with both immune-mediated demyelinating episodes and slowly progressive neurodegeneration within the central nervous system. Axonal degeneration is also evident within the retina of MS patients. Furthermore, the degeneration of retinal cells can precede clinical evidence of decline. Thus, developing and applying advanced technologies to study the retina could improve understanding of the pathobiology of MS and provide clinically valuable biomarkers of disease progression.

Three technologies can be applied to the patient population to achieve the goal. First, Optical Coherence Tomography (OCT) is a method that non-invasively quantifies the structure of the retina at the cellular level and can be used to measure the peripapillary retinal nerve fiber layer (RNFL) thickness, which correlates with axonal preservation. Second, the system 100 including light stimulus measures retinal vessels down the capillary level. Preliminary studies have found associations between vascular bed changes and neurological function in multiple sclerosis as well as neurodegenerative diseases. Third, pupillography is a technique that measures pupil reactivity to light. Pupil reactivity correlates not only with structural metrics of the retina in patients with MS, but also with metrics of fatigue and mood. Traditional pupillometry uses white light to stimulate the retina broadly. However, the method included specifically stimulating specialized retinal cells called intrinsically photosensitive retinal ganglion cells (ipRGCs) that have unique biologic properties and connections to the hypothalamus. Multichromatic pupillography can be used to measure light reactivity specifically correlated with ipRGCs. By selectively stimulating the photoreceptors that compose this tract, their function can be isolated and quantified.

Thus, the system and method of the present inventive concept advantageously enables a user to understand and quantify neuronal structure via OCT, neuronal function (via selective pupillography) and vascular structure. Applying these technologies to MS provides an opportunity to quantify progression within patients and to correlate structure function changes with common symptoms of MS. Sleep disorders are a very common issue in progressive MS, which is characterized by progressive degeneration independent of disease relapses. Therefore, in those patients, axon loss can be documented by an annual measure of the RNFL thickness. A significant amount of data suggest that both axonal degeneration and vascular dysfunction play a role in the pathogenesis of progressive MS. Investigating the underlying mechanisms of progressive MS in the visual system is useful because many of the proposed mechanisms can be exquisitely localized both functionally and structurally. Multichromatic pupillography results may correlate with MS patient symptoms, while OCT and OCT-A derived longitudinal changes with light stimulus may correlate with overall disability in MS progression.

A longitudinal study was conducted on the visual system to gain insight into the mechanisms and dynamics of neurodegeneration in multiple sclerosis. The majority of studies utilizing OCT to interrogate MS have focused on quantifying retinal cellular structures, but have not adequately examined the role of vascular biology in MS progression.

Despite increasing number of people diagnosed with the progressive forms of MS, there is no diagnostic test for the condition. The often-cited 2013 Lublin criteria state that the diagnostic criteria is a progressive functional objective deficit in the absence of relapse. The lack of specificity of the diagnostic criteria and the lack of quantifiable biomarkers of progression create an obstacle for well-designed and interpretable therapeutic clinical trials. Determining the efficacy of a therapeutic agent requires huge investments in prolonged clinical trials. These efforts could be improved if a reliable biomarker of neurodegeneration could be validated.

Much of the limitations on the diagnostic criteria of the disease is driven by the lack of knowledge on the pathogenesis of progressive disease. Animal models for the disease are confounded by the heterogeneity of mechanisms and pathophysiology. Much of the current human subject research has focused on utilizing Magnetic Resonance Imaging (MRI) as a tool to understand the pathophysiology of the condition. Despite multiple sclerosis being a white matter disease, grey matter volume rather than white matter volume, both in cross sectional and cohort studies, correlate best with disability accumulation (and hence progressive forms of the disease). Fascinatingly, in brain volumetric studies, ischemic risk factors such as tobacco exposure, and obesity, also increase the risk of brain atrophy, raising issues about interpretation and specificity of MRI metrics as a diagnostic tool. Efforts to refine the technology are ongoing, including post mortem studies.

The role of a vasculopathy in neurodegenerative disorders in general has been increasingly recognized. Brain atrophy rates in patients without neurological disease, Alzheimer disease, and multiple sclerosis have been repeatedly shown to be dependent on vascular risk factors. In multiple sclerosis vascular density as measured by OCT-A correlated better with a disability metric incorporating cognition than the ganglion cell layer plus inner plexiform layer (GCL+ IPL) thickness. While factors such as diabetes, hypertension, and obesity have shown a relationship with brain atrophy, whether this influence is purely volume based on a direct vasculopathy is yet to be determined. As examination of the microvasculature is beyond the voxel limits of clinical MRI, using the technologies of neuro-ophthalmology becomes an attractive opportunity. It remains to be seen if vascular changes in MS contribute to progression of the disease or if progressive loss of neurons leads to a small vascular bed due to a reduced perfusion requirement.

In postmortem studies of multiple sclerosis, nearly 100% of patients display disease at the level of the optic nerve and/or retina, making it an attractive focus for the development of specific diagnostic testing. Indeed, this is an active field of research, from both a diagnostic and therapeutic standpoint, with recent studies reevaluating the diagnostic criteria for the disease itself to consider inclusion of retinal imaging. Utilizing OCT to quantify direct cellular and axon metrics reveals strong correlations with disability, but also with visual metrics and cognitive metrics. Using the system 100 with light stimulus to quantify vascular density offers the advantage of isolating vascular contributions to the disease process. Specifically investigating relative rates of loss across the spectrum of a disease can offer insight into whether this is a primary or secondary process. Retinal thinning may lead to a reduction in the vascular network due to decreased perfusion needs. While MRI data suggests there may be a vascular component in multiple sclerosis, what is in progressive multiple sclerosis is not yet determined. It is desirable to leverage the visual system to parse out and localize this dysfunction at the cellular level.

Pupillography has been shown to be sensitive to a number of physiologic signatures, including cognition, sleepiness, mood, and in functional optic neuropathies. However, most of the research has used pan retinal stimulation. Multichromatic pupillography offers the ability to isolate certain retinal pathways, such as those driven by rods, cones, or intrinsically photosensitive retinal ganglion cells (ipRGCs). Over the last two decades, much has been learned about the ipRGCs, and their role in optic pathways. Not only have ipRGCs been shown to be the major determinant in pupillary statics, but with the cellular subtypes of opsin targeting separate pathways, these separate pathways can be functionally isolated and measured in vivo.

The melanopsin-containing ipRGCs and their associated tracts have been shown to play a major role in numerous diseases. Shifts in the pupillary responses have been described in those patients suffering from seasonal affective disorder, depression, diabetes, and neurodegenerative conditions such as Alzheimer disease and Parkinson disease. Dysfunction of ipRGCs and their correspondingly driven retinohypothalamic tract is responsible for phase shifts in setting the circadian rhythm of the suprachiasmatic nucleus. The subsequent dysfunction of the hypothalamus could be responsible for the commonly observed sleep dysregulation, mood dysregulation as well as temperature dysregulation seen in multiple sclerosis.

The ipRGCs have shown to be relatively resistant to damage in toxic and genetic optic neuropathies, but loss of ipRGCs density correlates well with age. In patients with severe vasculopathies such as diabetic retinopathy there is a remarkable reduction in the number of ipRGCs, indicating these cells are uniquely connected to the vasculature. Coupling the ipRGC mediated pupillary response with granular vascular studies via OCT-A offers a window to understanding a possibly common pathophysiology. Neurodegenerative disorders including Alzheimer disease have revealed enlargement of the foveal avascular zone, as well as retinal thinning compared to their non-diseased age-match controls. As the retina is embryologically close to the thalamus, utilizing retina as window into the brain has been informative for the study of these disorders. Similarly, dysfunction of the ipRGCs, coupled with vascular dysfunction, could yield insight into a number of neurodegenerative disorders.

Understanding the role of ipRGCs in disease is confounded by the heterogeneity in its response. Isolating this cellular population from the rest of the retina can help determine their contribution to metrics of neurodegeneration and correlation with patient symptoms. MS provides a unique opportunity to study this complex biology. The function of the pathway is related to some of the most important clinical aspects of progressive multiple sclerosis, including cognition, insomnia, and fatigue.

Beyond physical disability, fatigue is the most common, and debilitating complaint of patients with multiple sclerosis. Coupled with the vascular data, a corollary of our theory is that the reduced vascular network leads to dysfunction of the metabolically active ipRGCs, leading to fatigue symptomology in multiple sclerosis. Elucidating the role of the ipRGCs in multiple sclerosis provides a unique opportunity to further understand this challenging disease, and pave the way for a new wave of therapeutics, which may directly inform policy and practice by establishing effective diagnostic, prognostic and treatment related biomarkers.

The collection of granular visual data may not only develop a biomarker but simultaneously give insight into the pathophysiology of a neurodegenerative disease. Also, the systems and methods of the present inventive concept provide a unique opportunity to localize the functionality of the retinohypothalamic tract in vivo. As fatigue is the most common complaint patients with multiple sclerosis, and retinal disease exists across the continuum in the same patient population, this is a unique opportunity to take both the structure and a functional measure to correlate with reliable patient metrics such as sleep onset latency (SOL) and patient-centered outcomes.

Any ranges cited herein are inclusive. The terms "substantially" and "about," as used herein, are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the method and system, which, as a matter of language, might be said to fall therebetween.

What is claimed is:

1. A method of quantifying retinal blood flow in a retinal vasculature, the method comprising:

measuring a vascular density of a baseline retinal vasculature to obtain a baseline vascular density;

stimulating the baseline retinal vasculature for a predetermined period of time using a blue light from a blue light source to form a blue light-stimulated retinal vasculature;

measuring a vascular density of the blue light-stimulated retinal vasculature to obtain a blue light-stimulated vascular density; and quantifying retinal perfusion in the retinal vasculature by quantifying a vascular density change between the baseline vascular density and the blue light-stimulated vascular density.

2. The method of claim 1, wherein the retinal vasculature is modulated by intrinsically photosensitive retinal ganglion cells (ipRGCs).

3. The method of claim 1, wherein the retinal vasculature comprises a choriocapillaris.

4. The method of claim 1, wherein, the measuring of the vascular density of the baseline retinal vasculature and the measuring of the vascular density of the blue light-stimulated retinal vasculature include scanning the baseline retinal vasculature and the blue light-stimulated retinal vasculature to obtain one or more 3D images of the baseline retinal vasculature and one or more 3D images of the blue light-stimulated retinal vasculature, and the quantifying of the vascular density change includes comparing the one or more 3D images of the baseline retinal vasculature to the one or more 3D images of the blue light-stimulated retinal vasculature.

5. The method of claim 4, wherein the vascular density of the baseline retinal vasculature and the vascular density of the blue light-stimulated retinal vasculature are measured using optical coherence tomography angiography.

6. The method of claim 1, wherein the vascular density change stimulated by the blue light is at least 6% relative to the baseline vascular density.

7. The method of claim 6, wherein the vascular density change stimulated by the blue light is at least 8% relative to the baseline vascular density.

8. The method of claim 1, wherein the blue light source is a light-emitting diode (LED) light source.

9. The method of claim 1, wherein the predetermined period of time is at least 1 second.

10. The method of claim 1, wherein the blue light has a wavelength of 440 nm to 495 nm.

11. The method of claim 10, wherein the blue light has a wavelength of 463 nm.

12. The method of claim 1, wherein the baseline vascular density comprises one or more measurements of the baseline retinal vasculature that has not been stimulated by light.

13. A method of diagnosing a neurodegenerative disease in a subject, the method comprising:

providing the quantification of retinal perfusion of the subject according to the method of claim 1;

comparing the retinal perfusion of the subject to one or more threshold values; and when the retinal perfusion is a value above or below the one or more threshold values, determining the retinal perfusion is indicative of the neurodegenerative disease in the subject.

14. The method of claim 13, wherein the neurodegenerative disease is Multiple Sclerosis, Alzheimer's Disease, or Parkinson's Disease.

15. A method of diagnosing a neurodegenerative disease in a subject, the method comprising:

providing the quantification of retinal perfusion of the subject according to the method of claim 1;

comparing the retinal perfusion of the subject to a training data set by using a machine learning algorithm to yield a comparison, the training data set including retinal perfusion in positive individuals diagnosed with the neurodegenerative disease and retinal perfusion in negative individuals diagnosed as not having the neurodegenerative disease;

classifying the retinal perfusion of the subject as positive or negative based on the comparison; and diagnosing the neurodegenerative disease in the subject based on the classification.

*     *     *     *     *